US012605525B2

(12) United States Patent
Thakor et al.

(10) Patent No.: US 12,605,525 B2
(45) Date of Patent: Apr. 21, 2026

(54) FOCUSING CATHETER

(71) Applicant: NEXTERN INNOVATION, LLC, St. Paul, MN (US)

(72) Inventors: Avnesh Thakor, Menlo Park, CA (US); John D. Foley, Libettyville, IL (US); Ryan Douglas, Stillwater, MN (US)

(73) Assignee: Nextern Innovation, LLC, Maple Grove, MN (US)

( * ) Notice: Subject to any disclaimer, the term of this patent is extended or adjusted under 35 U.S.C. 154(b) by 1240 days.

(21) Appl. No.: 17/110,588

(22) Filed: Dec. 3, 2020

(65) Prior Publication Data

US 2021/0170143 A1 Jun. 10, 2021

Related U.S. Application Data

(60) Provisional application No. 62/943,510, filed on Dec. 4, 2019.

(51) Int. Cl.
　A61M 25/01 (2006.01)
　A61M 25/00 (2006.01)

(52) U.S. Cl.
　CPC .... A61M 25/0122 (2013.01); A61M 25/0026 (2013.01); A61M 2025/0039 (2013.01)

(58) Field of Classification Search
　CPC ................ A61M 25/00; A61M 25/001; A61M 25/0021; A61M 25/0026; A61M 25/0028; A61M 25/0029; A61M 25/003; A61M 25/0032; A61M 25/0043; A61M 25/0067; A61M 25/0068; A61M 25/0071; A61M 25/0082; A61M 25/0097; A61M 25/0122;
(Continued)

(56) References Cited

U.S. PATENT DOCUMENTS 3,416,730 A * 12/1968 Perry ...................... B05B 7/061
　　　　　　　　　　　　　　　　　　　　　239/416.5
6,597,438 B1 7/2003 Cabuz et al.
(Continued)

OTHER PUBLICATIONS

Hector Nolla, Basic Principles in Flow Cytometry, University of California, Berkeley, 2016.
(Continued)

*Primary Examiner* — Kevin C Sirmons
*Assistant Examiner* — Alexandra Lalonde
(74) *Attorney, Agent, or Firm* — Definitive Patents, member Synchrony IP; Timothy D. Snowden; Yau H. Chan

(57) ABSTRACT

Apparatuses and associated methods relate to a coaxial stream delivery device having an inlet section and an outlet section in fluid communication via a plenum chamber. In an illustrative example, an inner radius of the plenum chamber may monotonically decrease distally along a longitudinal axis. The inlet section may include an inner tubular wall extending along the longitudinal axis. At least one bridge may extend radially inward from the inner tubular wall to coaxially align an inner conduit within the inner tubular wall relative to the longitudinal axis. The at least one bridge may define a annular sector apertures bounded by the inner tubular wall and an outer wall of the inner conduit. Various embodiments may advantageously be disposed in a fluid path to coaxially align a therapeutic fluid stream entering the inner conduit within a sheath fluid stream entering the annular sector apertures.

19 Claims, 5 Drawing Sheets

(58) Field of Classification Search

CPC ...... A61M 25/0023; A61M 2025/0004; A61M 2025/0006; A61M 2025/0034; A61M 2025/0037; A61M 2025/0039; A61M 2025/004; A61M 2025/0042; A61M 2025/0057; A61M 2025/0059; A61M 2025/0073; A61M 2025/0096; A61M 5/1582; A61M 5/30; A61M 5/3007; A61M 39/08; A61M 39/105; A61M 39/10; A61M 2039/082; A61M 2039/0211; A61M 2039/0214; A61M 25/01; A61M 25/0105; B05B 7/061; B05B 1/002; B05B 7/06; B05B 7/066; A61B 17/3203; B01F 33/3011

See application file for complete search history.

(56) References Cited

U.S. PATENT DOCUMENTS

| | | | |
|---|---|---|---|
| 6,758,828 | B2 | 7/2004 | Hammer et al. |
| 7,311,476 | B2 | 12/2007 | Gilbert et al. |
| 8,182,444 | B2 | 5/2012 | Uber, III et al. |
| 8,263,387 | B2 | 9/2012 | Pagano et al. |
| 8,563,325 | B1 | 10/2013 | Bartsch et al. |
| 9,588,100 | B2 | 3/2017 | Appleyard et al. |
| 9,855,386 | B2 | 1/2018 | Close et al. |
| 10,254,212 | B2 | 4/2019 | Ward et al. |
| 10,632,281 | B2 | 4/2020 | Rosenman et al. |
| 2005/0123450 | A1* | 6/2005 | Gilbert ..................... B07C 5/00 |
| | | | 422/81 |
| 2005/0245896 | A1 | 11/2005 | Kucharczyk et al. |
| 2010/0160897 | A1* | 6/2010 | Ducharme .......... A61M 5/1409 |
| | | | 604/82 |
| 2012/0301883 | A1 | 11/2012 | Pagano et al. |
| 2013/0144207 | A1* | 6/2013 | Gonon ............... A61M 3/0275 |
| | | | 604/70 |
| 2017/0086707 | A1 | 3/2017 | Mahapatra et al. |
| 2017/0281870 | A1* | 10/2017 | Kai ...................... B05B 7/2472 |

OTHER PUBLICATIONS

Huber, et al., Hydrodynamics in Cell Studies, Chem. Rev. 2018, 118, 2042-2079.

* cited by examiner

FOCUSING CATHETER

CROSS-REFERENCE TO RELATED APPLICATIONS

This application claims the benefit of U.S. Provisional Application Ser. No. 62/943,510, titled "Focusing Catheter," filed by Avnesh Thakor, et al., on Dec. 4, 2019.

This application incorporates the entire contents of the foregoing application(s) herein by reference.

TECHNICAL FIELD

Various embodiments relate generally to delivery of fluid streams from a plurality of sources as coaxial streams within a single conduit.

BACKGROUND

Various therapies may, for example, involve fluid therapy to a patient. Fluid therapy may be implemented, for example, to correct dehydration, intravascular volume control, electrolyte disturbances, redistribution of fluids, and inadequate perfusion. Fluid therapy may be delivered, by way of example and not limitation, via oral delivery, subcutaneous delivery, intravascular delivery, intravenous delivery, intramuscular delivery, intraosseous delivery, intrathecal delivery, intraperitoneal delivery, intracardiac delivery, intraarticular delivery, intravitreal delivery, percutaneous delivery, intratissue infusion, or some combination thereof.

Fluid therapy may be delivered via, for example, catheters, fluid lines, ports, intravenous bags, syringes, bottles, needles, or some combination thereof. Fluid therapy may include one or more therapeutic agents. Fluid therapy may, for example, deliver one or more therapeutic agents to one or more target tissues.

SUMMARY

Apparatus and associated methods relate to a coaxial stream delivery device having an inlet section and outlet section in fluid communication via a plenum chamber. In an illustrative example, an inner radius of the plenum chamber may monotonically decrease distally along a longitudinal axis. The inlet section may include an inner tubular wall extending along the longitudinal axis. At least one bridge may extend radially inward from the inner tubular wall to coaxially align an inner conduit therewithin relative to the longitudinal axis. The at least one bridge may define a corresponding number of annular sector apertures bounded by the inner tubular wall and an outer wall of the inner conduit. Various embodiments may advantageously be disposed in a fluid path to coaxially align a therapeutic fluid stream entering the inner conduit within a sheath fluid stream entering the annular sector apertures.

Various embodiments may achieve one or more advantages. For example, some embodiments may advantageously deliver therapeutic agents within a sheath stream to a target tissue. The sheath stream may, for example, reduce shear stress on therapeutic agents (e.g., cells) within a therapeutic stream. Various embodiments may, for example, advantageously deliver a therapeutic stream including a suspension of individual and/or grouped cells. Various embodiments may advantageously deliver cells in a therapeutic stream in single file. Various embodiments may advantageously permit use of standard fluid line components (e.g., catheters, luer fittings, ports, and fluid lines) to deliver cellular-based therapies. Various embodiments may, for example, advantageously permit sheath fluid and therapeutic fluid to be dispensed from individual reservoirs and converged inline within the coaxial stream delivery device such that the therapeutic fluid stream is coaxially aligned within the sheath fluid stream and delivered to a target tissue via a single lumen conduit.

The details of various embodiments are set forth in the accompanying drawings and the description below. Other features and advantages will be apparent from the description and drawings, and from the claims.

BRIEF DESCRIPTION OF THE DRAWINGS

Like reference symbols in the various drawings indicate like elements.

DETAILED DESCRIPTION OF ILLUSTRATIVE EMBODIMENTS

Figure 3:
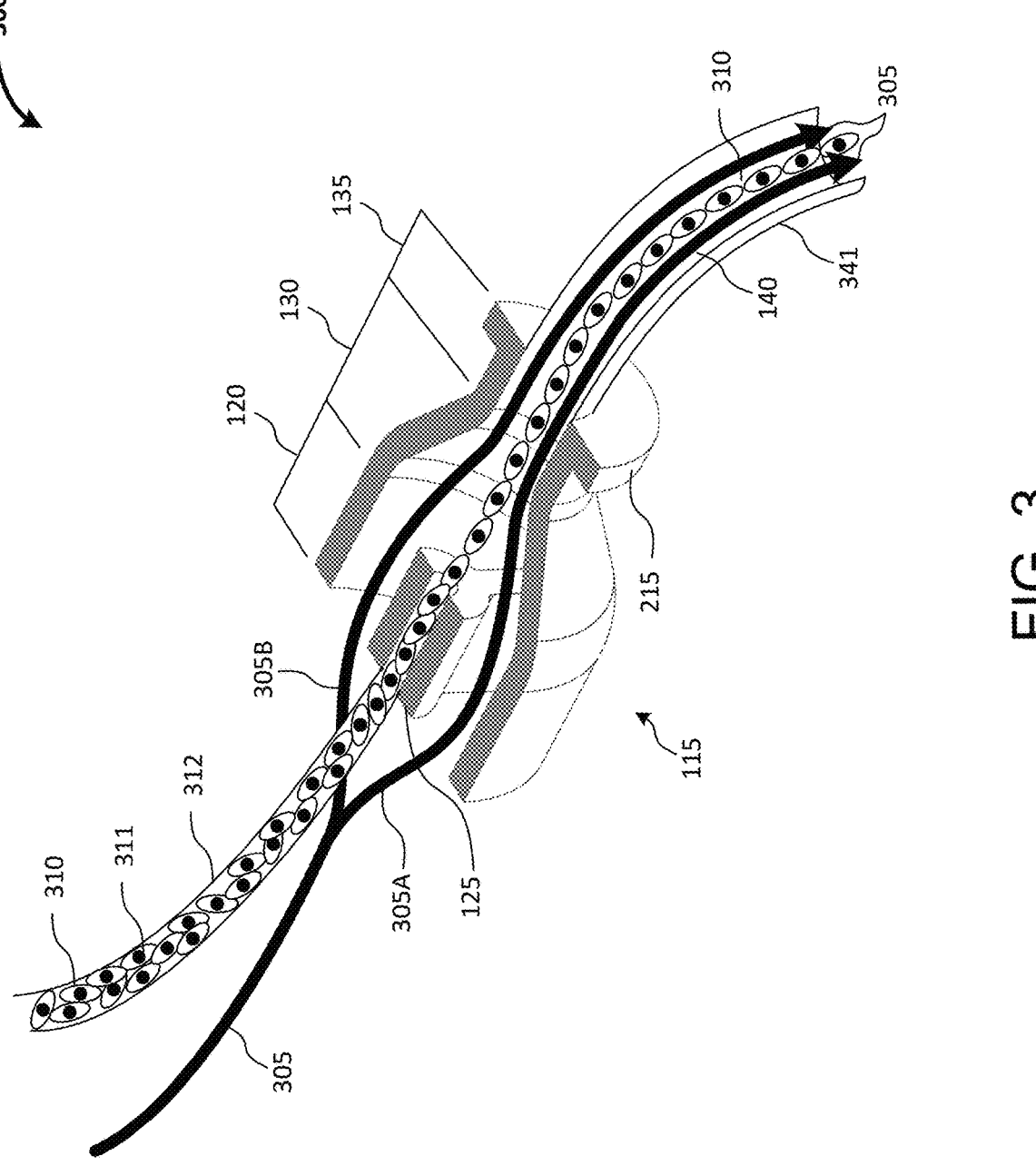
FIG. 3 depicts illustrative operation of the exemplary CSDD of FIGS. 2A-2B to coaxially center a therapeutic cell stream within a sheath stream in a single delivery conduit.
Figure 4:
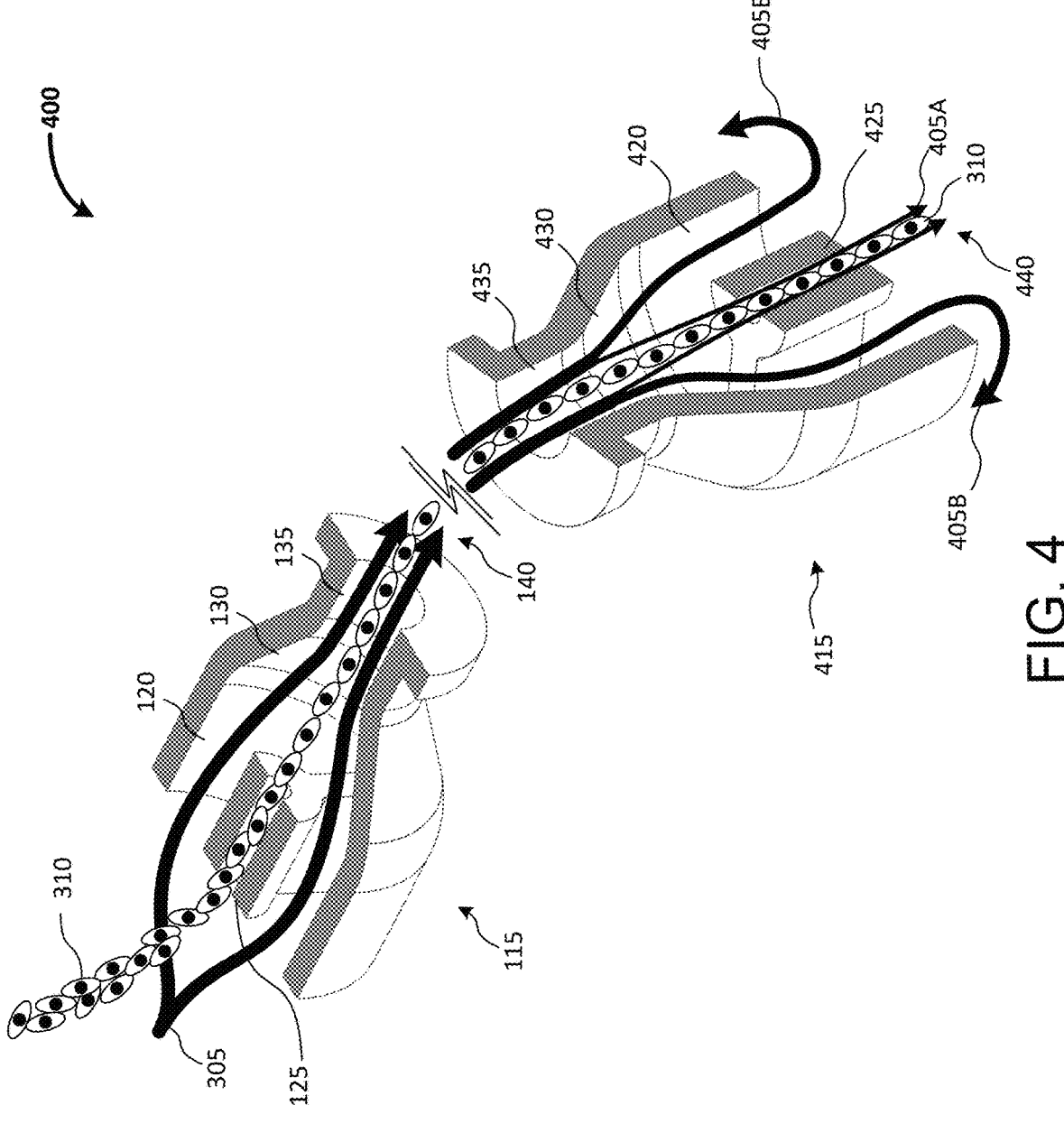
FIG. 4 depicts illustrative operation of the exemplary CSDD of FIG. 3 provided with a second downstream CSDD configured to provide sheath stream reduction.

To aid understanding, this document is organized as follows. First, to help introduce discussion of various embodiments, an exemplary coaxial stream delivery system is introduced with reference to FIG. 1. Second, that introduction leads into a description with reference to FIGS. 2A-2C of an exemplary embodiment of a CSDD. Third, with reference to FIGS. 3-4, illustrative operation of a CSDD is described. Finally, the document discusses further embodiments, exemplary applications and aspects relating to coaxial stream delivery.

Figure 1:
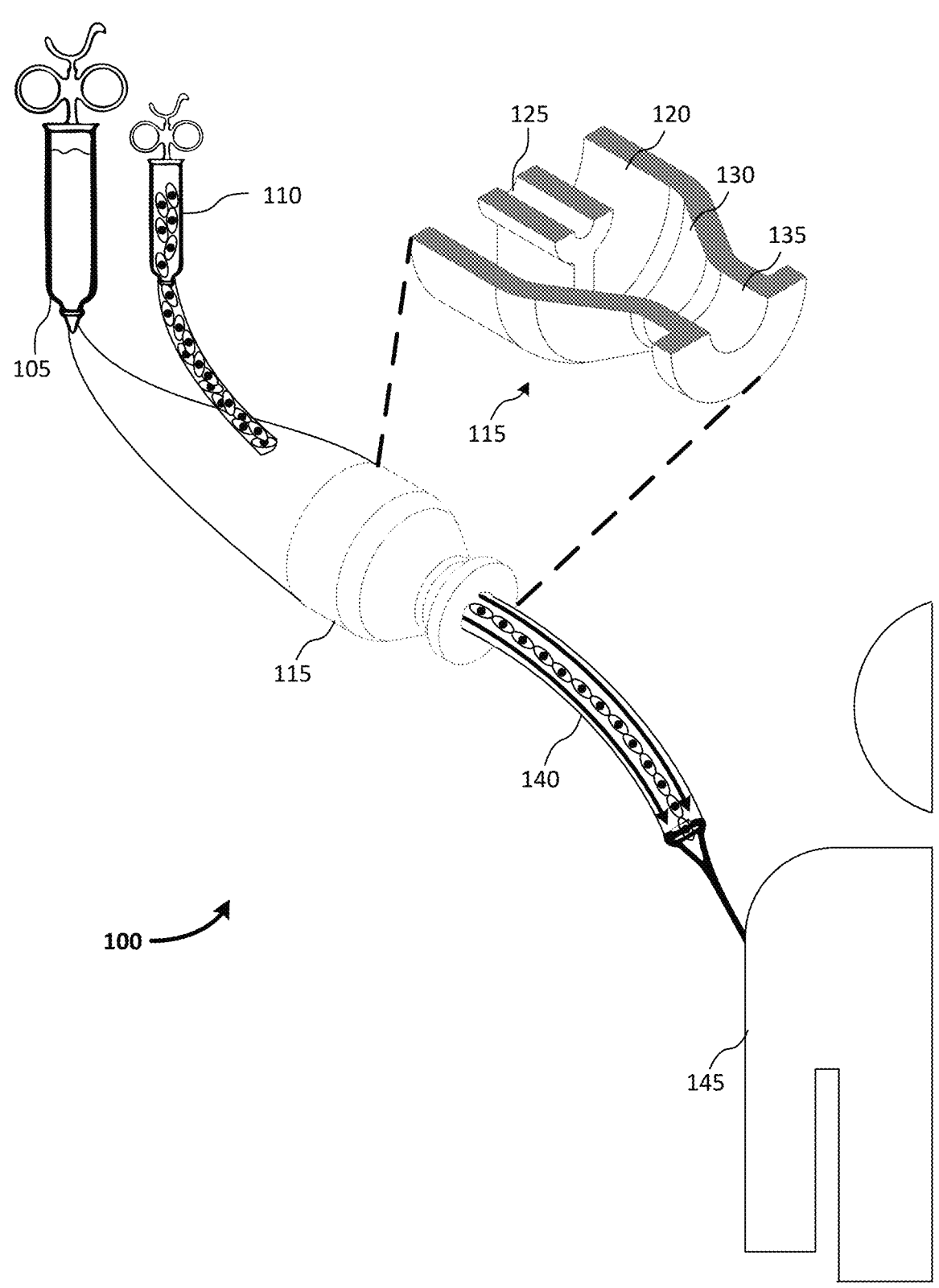
FIG. 1 depicts an exemplary inline coaxial stream delivery device (CSDD) in an illustrative use case of in vivo delivery of a therapeutic cell stream coaxially centered within a sheath stream.

FIG. 1 depicts an exemplary inline coaxial stream delivery device (CSDD) in an illustrative use case of in vivo delivery of a therapeutic stream coaxially centered within a sheath stream. In the depicted example, the therapeutic stream includes individual cells. Various embodiments may, by way of example and not limitation, include cells (individual and/or in groups) and/or non-cellular therapeutic agent(s). In the depicted exemplary system 100, sheath fluid and therapeutic fluid are dispensed from individual dispensing reservoirs 105 and 110, respectively. CSDD 115 is disposed inline downstream from the dispensing reservoirs 105 and 110.

CSDD 115 includes an inlet section 120, a plenum chamber 130, and an outlet section 135. The sheath fluid stream is received into inlet section 120. The therapeutic fluid stream is received into a lumen of inner conduit 125. The therapeutic fluid stream and sheath fluid stream converge in plenum chamber 130 such that the therapeutic fluid stream is hydrodynamically centered within the sheath fluid stream to form coaxial fluid stream 140. Coaxial fluid stream 140 exits outlet section 135 and is delivered from thence through a delivery conduit into target tissue of patient 145. Accordingly, various embodiments may advantageously provide a protective fluid sheath around a therapeutic fluid stream.

In various embodiments, the sheath fluid stream may include, by way of example and not limitation, isotonic saline, or other biocompatible carrier and shielding fluid. The sheath stream may, for example, advantageously shield the therapeutic fluid stream from deleterious shear stress during delivery. The therapeutic stream may include a supply of therapeutic agents (e.g., cells) delivered serially, for example, in single file fashion. In various embodiments the coaxial stream may, by way of example and not limitation, advantageously reduce shear forces on potential therapeutic agents (e.g., therapeutic cells); reduce the potential for clumping of therapeutic agents that could cause vascular occlusions; and/or improve dosage control.

Figures 2A, 2B:
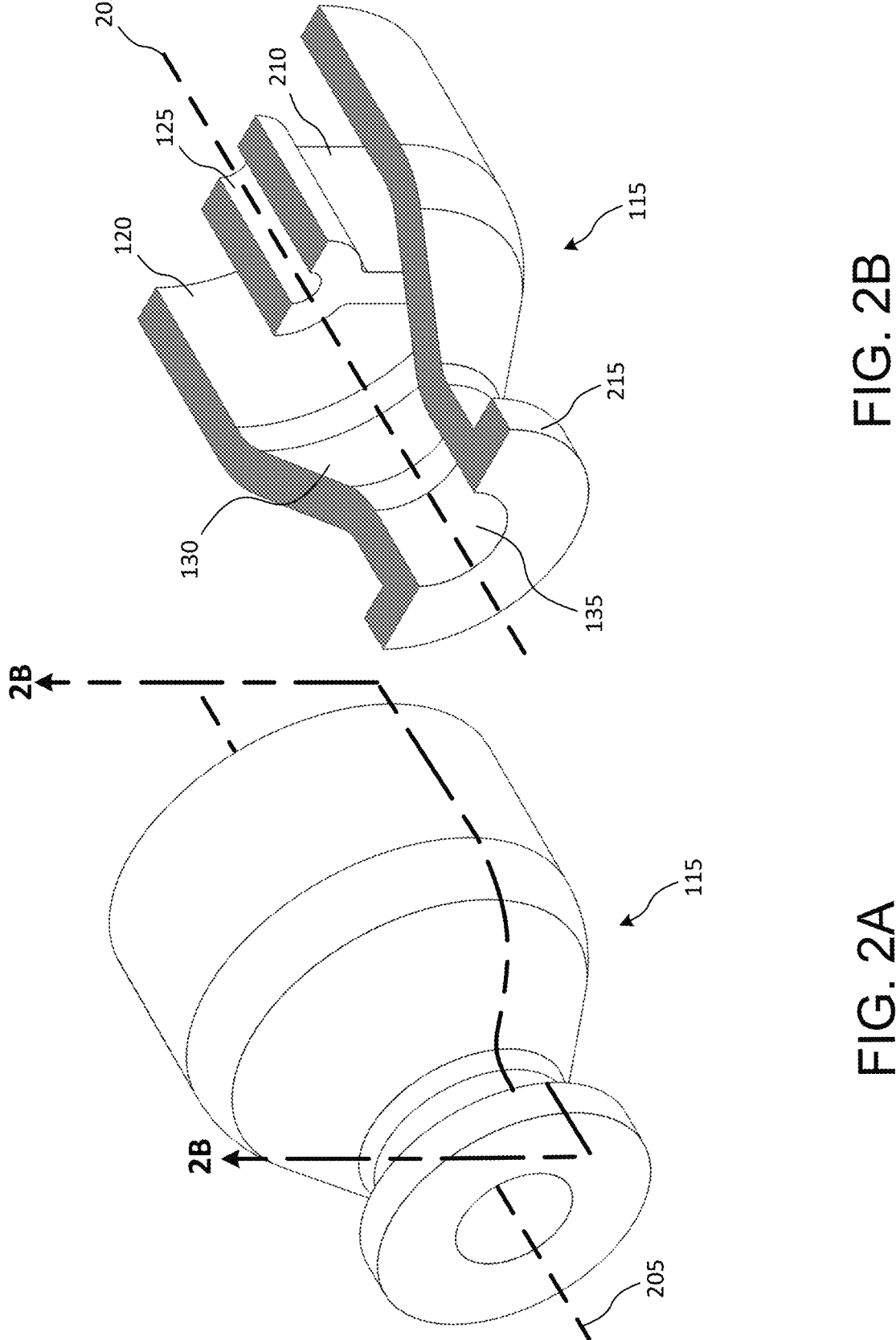
FIG. 2A depicts a perspective view of an exemplary CSDD.
FIG. 2B depicts a section of the exemplary CSDD of FIG. 2A.
Figure 2C:
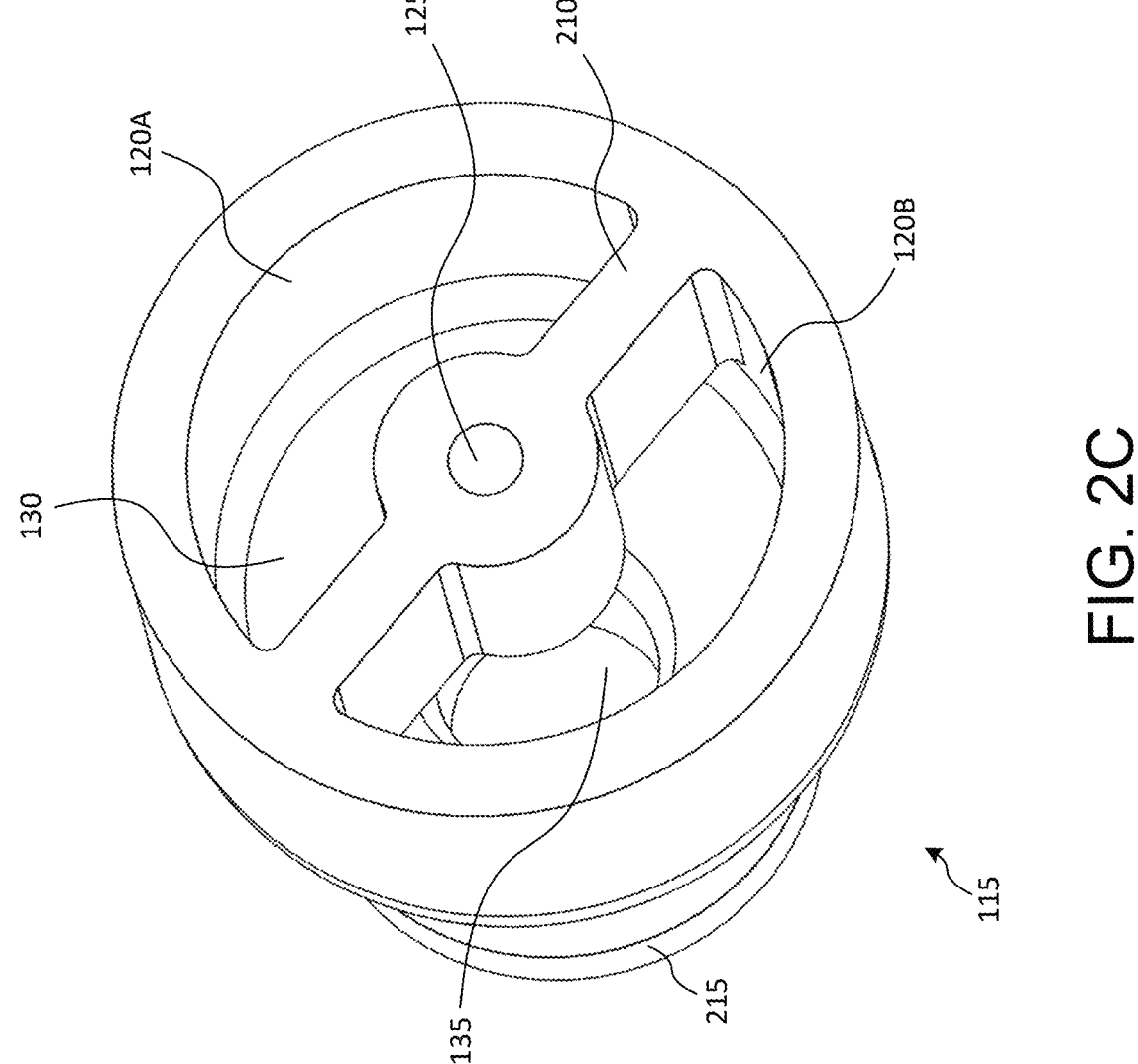
FIG. 2C depicts a second perspective view of an exemplary CSDD.

FIG. 2A depicts a perspective view of an exemplary CSDD. FIG. 2B depicts a section of the exemplary CSDD of FIG. 2A along cutting line 2B. FIG. 2C depicts a second perspective view of an exemplary CSDD. Depicted CSDD 115 is substantially radially symmetric about longitudinal axis 205. The CSDD 115 includes three subsequent sections: inlet section 120, plenum chamber 130 and outlet section 135. An inner lumen 125 is centered concentrically within inlet section 120 by N bridges 210, where N is greater than or equal to one. In the depicted example, N=2. The two bridges 210 extend radially from an inner wall of inlet section 120 to an outer wall of inner conduit 125. The bridges 210, inner wall of inlet section, and outer wall of inner conduit 125 form N annular sector apertures 120A and 120B into corresponding annular sector lumens. As depicted, the annulus sectors may be of constant radius relative to the longitudinal axis 205.

Accordingly, a sheath fluid stream may be received through the annular sector apertures 120A and 120B and a therapeutic fluid stream may be received through the inner conduit 125, coaxially converged in plenum chamber 130, and dispensed as a coaxial stream out of outlet section 135. The annulus sectors may, for example, advantageously hydrodynamically center the therapeutic stream in a constant thickness sheath of the sheath fluid. Accordingly, therapeutic flow may be, for example, advantageously delivered through substantially cylindrical flow paths (e.g., standard catheter sets, needles, and/or luer fittings) which may not be shear-optimized (e.g., standard luer fittings with sharp transition points).

FIG. 3 depicts illustrative operation of the exemplary CSDD of FIGS. 2A-2B to coaxially center a therapeutic stream within a sheath stream in a single delivery conduit. Exemplary system 300 depicts sheath fluid stream 305 and therapeutic stream 310 entering inline CSDD 115. Sheath fluid stream 305 splits into first sheath fluid stream 305A and second sheath fluid stream 305B to enter the two annular sector apertures of inlet section 120 of CSDD 115. In the depicted example, therapeutic stream 310 is made up of therapeutic agents 311 (e.g., cells). Therapeutic stream 310 passes through conduit 312 into inner conduit 125 of inlet section 120. As depicted, the cells 311 (or other therapeutic agent(s)) are not in single-file before entering CSDD 115.

As the two independent streams 305 and 310 exit the inlet section 120 and converge inside plenum chamber 130, the monotonically decreasing radius of plenum chamber 130 may accelerate sheath fluid stream 305 such that therapeutic stream 310 is entrained coaxially therewithin upon exiting inner conduit 125 such that cells 311 are suspended in single-file in therapeutic stream 310. Accordingly, the concentric stream 140 exits outlet section 135 as an inner therapeutic stream 310 surrounded by an outer sheath fluid stream 305 of substantially constant thickness. The concentric stream 140 is conveyed through delivery conduit 341. Delivery conduit 341 may, by way of example and not limitation, be provided at a proximal (upstream) end with a luer fitting which may releasably couple the delivery conduit 341 to the luer fitting 215 of the CSDD 115. Accordingly, a therapeutic stream may be, for example, advantageously delivered in a shear reducing protective sheath.

FIG. 4 depicts illustrative operation of the exemplary CSDD of FIG. 3 provided with a second downstream CSDD configured to provide sheath stream reduction. In exemplary system 400, a converging CSDD 115 receives the sheath stream 305 into the inlet section 120 and the therapeutic flow 310 into the inner conduit 125 of the inlet section 120. The sheath stream 305 converges in the plenum chamber 130 and coaxially entrains the therapeutic stream 310 therewithin. The resulting concentric stream 140 exits the outlet section 135.

Downstream from the converging CSDD 115, a sheath reducing CSDD 415 is positioned. As depicted, the reducing CSDD 415 is oriented in-line with the concentric stream 140 and reflected about a plane normal thereto relative to the converging CSDD 115. The concentric stream 140 enters a second inlet section 435 and therefrom into a second plenum chamber 430. The plenum chamber 430 monotonically increases in radius relative to a longitudinal axis through the reducing CSDD 415. The plenum chamber opens into a second outlet section 420. A second inner conduit 425 is concentric with outlet section 420 and supported therewithin by M bridges (where M is greater than or equal to one), as described in relation to FIGS. 2A-2C.

In the depicted example, as concentric stream 140 enters outlet section 420, a portion 405B of outer sheath stream 305 is separated by inner conduit 425 and flows through M annular sector lumens defined by an inner wall of outer section 420, an outer wall of inner conduit 425, and the M bridges therebetween. The inner therapeutic stream 310 and a remaining portion 405A of the outer sheath stream 305 flows through inner conduit 425 and thence out as reduced concentric stream 440. Accordingly, various embodiments may advantageously reduce the volume of an outer sheath stream by separating a portion thereof off before delivering the resulting concentric stream to a target tissue.

In various embodiments the cross-sectional area of an inner lumen of the inner conduit 425 may, by way of example and not limitation, be greater than an inner lumen of the inner conduit 125. In various embodiments the total cross-sectional area of the M annular sector lumens of outlet section 420 may, by way of example and not limitation, be smaller than a total cross-sectional area of the N annular sector lumens of inlet section 120. In various embodiments one or more predetermined ratios may be used to establish a radius of the inner lumen of the inner conduit 125 relative to the inner lumen of the inner conduit 425, the total cross-sectional area of the M annular sector lumens of the outlet section 420 relative to the total cross-sectional area of the N annular sector lumens of the inlet section 120, or some combination thereof. In various embodiments, the one or more predetermined ratios, radii, and/or cross-sectional areas may, for example, be determined according to a predetermined ratio(s) between, by way of example and not limitation, some combination of the sheath fluid stream (e.g., 305), the removed sheath fluid stream (e.g., 405B), the retained sheath fluid stream (e.g., 405A), the therapeutic stream (e.g., 310), the reduced concentric stream (e.g., 440), and the concentric stream (e.g., 140). In various embodiments, relative dimensions may, by way of example and not limitation, be determined according to a maximum allowed shear stress, a maximum allowed volume delivered to the target tissue, geometry of a flow path, contents of the therapeutic stream and/or the sheath fluid stream, or some combination thereof.

In various embodiments, dimensions of components may be determined, for example, by sizes of therapeutic agents used. In various embodiments, a range of predetermined CSDD sizes and geometries, for example, may advantageously accommodate therapeutic agents of various sizes. Predetermined CSDDs may, by way of example and not limitation, be configured to advantageously coaxially align therapeutic agents in the sub-micron range (e.g. exosomes), in the tens of microns range (e.g. cells), in the hundreds of microns range (e.g. islet cells), in the millimeter range (e.g., therapeutics along with a carrier such as collagens, polymers, encapsulated agents), or some combination thereof. Predetermined sizing and/or geometry for a specific range of therapeutic agent(s) may, for example, include sizing and/or geometry of an inner conduit (e.g., 125 in FIG. 1), an inlet section (e.g., 120 in FIG. 1), and outlet section (e.g., 135 in FIG. 1). Predetermined dimensions may be adapted, for example, such that coaxial laminar flow of at least two streams (therapeutic and sheath) is maintained and the streams remain substantially separated.

In various embodiments a sheath reducing CSDD (e.g., 415) may, by way of example and not limitation, be configured to remove a portion of a sheath flow prior to delivery of the concentric stream into a target tissue. The rejected portion of the sheath flow may, for example, be discarded, recycled, collected, or otherwise disposed of. In some embodiments, for example, the rejected sheath flow may be converged into a fluid conduit.

In various such embodiments, for example, a relatively high-volume sheath flow may be used to entrain the therapeutic suspension. However, the volume of sheath flow may be, for example, undesirable or even detrimental for in-vivo delivery. Accordingly, one or more exit ports may be provided which reduce the volume of the sheath flow prior to delivery into tissue. By way of example and not limitation, a reduction in delivery lumen diameter (e.g., a reduction of catheter size) may coincide with one or more exit ports, allowing excess sheath fluid to be "stripped off" and reduce the volume of fluid delivered to the tissue. The exit port(s) may, for example, be positioned prior to entering tissue (e.g., to maintain a relatively "thick" protective sheath down the length of a delivery catheter until just prior to delivery to advantageously maximize protection), or some other desirable point prior to delivery.

Although various embodiments have been described with reference to the figures, other embodiments are possible. For example, in various embodiments an outlet section may for example, terminate in a luer connection (e.g., a male luer connection) suitable for releasable coupling of a standard luer connection thereto (e.g., a needle or catheter). The outer sheath stream may, for example, advantageously prevent damage to therapeutic agents in the therapeutic stream or disruption of concentric laminar flow of the therapeutic stream as it passes through the fluid path, including one or more luer connections. For example, many standard luer connections may include abrupt corners and/or edges. A standard luer coupling may, for example, introduce a pocket in the flow path where a blunt tip of a male luer connection ends within the lumen of a female luer fitting, thereby creating a disturbance and/or increased shear stress in the fluid path thereat. The outer sheath stream of a concentric fluid stream may, for example, advantageously reduce or substantially eliminate the effect thereof on the interior therapeutic stream.

In various embodiments, therapeutic and/or sheath fluid may be provided to an inlet section from various sources including, by way of example and not limitation, bags and/or syringes. For example, one bag or syringe may serve as a source of the sheath fluid and a separate bag or syringe for the therapeutic fluid. In implementations that use bag delivery, for example, fluid motive power may be provided by, for example, by pump(s), gravity, and/or bag compression. By way of example and not limitation, fluids may be started simultaneously, the sheath fluid may be started before the therapeutic fluid in order to establish concentric laminar flow prior to the delivery of the therapeutic fluid, or the therapeutic fluid may be started first to establish separate concentric streams.

In implementations that use syringe delivery, for example, the fluids may be manually delivered by a multitude of features including but not limited to hand compression of the plunger. In some implementations, two syringes containing sheath fluid and therapeutic fluid, respectively, may be docked into a hand-held component configured to compress the plungers via a mechanical or electro-mechanical mechanism. The velocities of the two inlet streams may be at the same rate or varied with one of the streams at a faster rate of flow (e.g., by sizing of syringes, limiters, relative lumen sizing). In various examples, adjusting the independent streams rates or the collective stream flow rates at the inlet end as well as at the outlet end may be used to achieve desired separation of therapeutic agents in the therapeutic fluid.

In various embodiments, a CSDD (e.g., 115 in relation to FIG. 1) may, for example, be substantially radially symmetric about a longitudinal axis. In various embodiments, various internal fluid-carrying lumens (e.g., lumen of inner conduit 125, plenum chamber 130, outlet section 135) may be radially symmetric about the longitudinal axis, but the entire CSDD may be other than radially symmetric. In various embodiments, N and/or M may be 1, 2, 3, 4, 5, 6, or any desired quantity. In various embodiments, the bridges (e.g., 210 in relation to FIG. 2B) may be formed with a convex surface profile on one or both sides. In some embodiments, the bridges may decrease in thickness along a direction from the inlet section toward the plenum chamber and parallel to the longitudinal axis.

In various embodiments, a CSDD (e.g., 115 in relation to FIG. 1) may be unitarily formed. In various embodiments, a CSDD may be integrated into a therapeutic delivery device. The delivery device may, for example, be manually or electronically powered and/or controlled. In various such embodiments, syringes containing sheath fluid and therapeutic fluid, respectively, may be loaded into the delivery device and oriented in a predetermined position therein. An activation mechanism (e.g., a lever) may, for example, be configured to actuate respective plungers of the syringes at a controlled rate. The activation mechanism may, for example, be configured to actuate the plungers at a controlled rate relative to each other. In various embodiments, activation mechanism may be, by way of example and not limitation, manually actuated such as, for example, by a user gripping, squeezing, and or depressing a lever or other appropriate activation mechanism. Accordingly, the sheath fluid and therapeutic fluid may be advantageously dispensed through an inline CSDD to deliver the therapeutic fluid within a sheath stream to a target tissue.

In various embodiments, a CSDD (e.g., 115 in FIG. 1) may, by way of example and not limitation, be provided with a sensing means (e.g., optical sensor, electrical sensor, acoustic sensor) and a feedback mechanism component to allow for real-time monitoring and accurate delivery of a therapeutic dosage. Various such embodiments may, for example, advantageously allow therapy to be stopped when a predetermined dosage is reached. Various embodiments may, for example, advantageously allow therapy to be adjusted based on one or more detectable data points collected, prior, during, and/or after administering of the therapeutic dose according to, for example, one or more predetermined parameters (e.g., predetermined thresholds). Various embodiments may, for example, allow for stopping and restarting the therapy during delivery to multiple sites in a patient when a predetermined dosage is reached at each location.

In various embodiments, one or more sensors may be used to determine and initiate adjustment of delivery of a predetermined therapeutic dose to ensure the most effective dose is delivered. For example, embodiments providing an adjustment mechanism related to a predetermined therapeutic dose may advantageously ensure an optimum effective dose is delivered. Such implementations may, by way of example and not limitation, include at least one pressure gauge configured to sense backpressure. Backpressure may, for example, increase if clumping (e.g., of therapeutic agents) occurs in a CSDD (e.g., 115 of FIG. 1). The system may, for example, be configured to adjust one or more flow parameters of the system to reduce and/or eliminate the clumping, as determined by a corresponding change in back pressure.

In various embodiments, a plurality of sheath streams and/or therapeutic streams may be delivered. By way of example and not limitation, a plurality of inner and/or outer streams may be concentrically arranged, radially arranged, or some combination thereof. For example, a plurality of sheath streams may be disposed radially around one or more inner therapeutic streams. A plurality of sheath streams may be disposed concentrically, one within another. Similarly, a plurality of therapeutic streams may be disposed radially around a longitudinal axis, and/or may be disposed concentrically, one within another. In some embodiments, a plurality of concentric therapeutic streams may be separated from one another by one or more concentric sheath streams therebetween.

In various embodiments, at least one filter may be applied upstream of a CSDD in a therapeutic fluid path. The filter may, for example, advantageously prevent clumps of cells from clogging the CSDD. In various embodiments, one or more low surface energy coatings may be applied to therapeutic fluid reservoirs and/or fluid lines. The coatings may, for example, advantageously reduce adherence and, thereby, increase the effective dose delivered. Such coatings may include, by way of example and not limitation, perfluorinated coatings.

In various embodiments, therapeutic fluid may include various cellular and/or non-cellular therapeutic agents. Cellular therapeutic agents may, by way of example and not limitation, include pancreatic islet cells, adipose-derived mesenchymal stem cells (MSCs), cord blood-derived MSCs, ischemia-tolerant MSCs, mesenchymoangioblasts, bone marrow cells, bone marrow-derived stem cells (SCs), hematopoetic stem cells, neural SCs, dendritic cells, GAGAergic interneurons, retinal pigment epithelial cells of many origins, human embryonic SCs, cardiac progenitor cells, cardiosphere-derived cells, muscle precursor cells, muscle-derived cells, nasal cavity SCs, platelet-rich plasma, mesoblast SCs, decidual stromal cells, T cells of multiple origins (genetically modified or not), CD34+ cells, natural killer (NK) cells, tumor-infiltrating lymphocytes, iPSCs, oogonal SCs, parthenogetic SCs, limbal SCs, hepatocytes, Sr beta cells, alpha cells, paraxial mesoderm multipotent cells (P2MCs), immunomodulatory progenitor cells (iMP), discogenic cells, fibroblasts, non-bulbar dermal sheath cells, choroid plexus cells, "pathfinder" cells, placenta-derived cells, or some combination thereof. Cell nomenclature is not fully standardized, and cellular-related terms used herein may include 'colloquialisms' unique to certain researchers, research fields or regions.

In various embodiments therapeutic agent(s) may, by way of example and not limitation, include cells derived from any of the three mammalian germ layers, extra-embryonic cells, or some combination thereof. In various embodiments, cells may include any cell type(s) which a physician, veterinarian, researcher, or other user wishes to deliver in a single file fashion and/or where control of potential clumping is desired. In various embodiments, therapeutic stream (s) may include cell-derived therapeutics such as, by way of example and not limitation: exosomes from one or more cell sources, red blood cells (RBCs), RBCs genetically altered to express therapeutic proteins, RBCs that act as carriers of therapeutic agents, conditioned medium, other appropriate cell-derived therapeutics, or some combination thereof.

In various embodiments, multiple cell types may be administered simultaneously in one or more therapeutic streams. Various embodiments, for example, may be configured to co-administer alpha and beta cells. Various embodiments may be configured for other multi-cell type combinations which may be desired depending, for example, on design of a therapy and desired delivery of a therapeutic dose. In various embodiments, the therapeutic fluid may contain, by way of example and not limitation, a combination of cells and one or more of non-cellular therapeutics such as, for example, drugs, biologics, exosomes and/or conditioned medium.

In various embodiments, therapeutic agents may include, by way of example and not limitation: micelles, encapsulated agents, collagen and/or other extracellular matrix (ECM) components either singly or combined, polymers, collagen and/or other ECM components or polymers seeded with cells of any origin, collagen and/or other ECM components or polymers seeded with exosomes, or some combination thereof. In various embodiments, one or more therapeutic agents may be delivered via the sheath stream(s). Therapeutic agents delivered via the sheath stream may include, by way of example and not limitation: drugs, biologics, exosomes, and/or conditioned medium.

Various embodiments may be configured specifically for one or more therapeutic indications. Therapeutic indications may include, by way of example and not limitation: diabetes, cancers (including but not limited to solid tumors), autoimmune diseases, muscular degenerative diseases, neural degenerative diseases, spinal cord injuries, stroke, liver diseases, cardiovascular diseases, ocular diseases, osteoarthritis, orthopedic indications, chronic wounds, burns, or some combination thereof. Although exemplary devices and systems have been described with reference to the figures, other implementations may be deployed in other industrial, scientific, medical, commercial, and/or residential applications.

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A coaxial stream delivery device comprising:
an inlet section comprising:
(i) an inner tubular wall extending along a longitudinal axis to define an inner lumen;
(ii) an outer tubular wall extending along the longitudinal axis concentrically about the inner tubular wall; and
(iii) N bridges extending radially between the inner tubular wall and the outer tubular wall to define N corresponding annular sector apertures, where the N is at least one;
a source of cells coupled to an upstream end of the inner lumen; and
a plenum chamber defined within a plenum wall that extends distally along the longitudinal axis from a distal end of the inlet section, the plenum chamber in fluid communication with the inner lumen and the N corresponding annular sector apertures,
wherein:
the N annular sector apertures provide longitudinal fluid communication between a first supply conduit coupled to a proximal end of the inlet section and the plenum chamber,
an inner radius of the plenum wall monotonically decreases distally along the longitudinal axis,
an inner radius of the outer tubular wall and an outer radius of the inner tubular wall are substantially constant along the longitudinal axis,
the inlet section is configured to receive a sheath fluid stream through the N corresponding annular sector apertures and to receive through the inner lumen a therapeutic fluid stream comprising cells from the source of cells, such that,
the sheath fluid stream shields the therapeutic fluid stream such that deleterious shear stress to the cells is prevented; and
further comprising a downstream sheath reduction apparatus configured such that a volume of the sheath fluid stream is removed from the therapeutic fluid stream via at least one exit port prior to delivery of the therapeutic fluid stream.

2. The coaxial stream delivery device of claim 1, wherein:
the therapeutic fluid stream is configured to exit the plenum chamber coaxially centered within the sheath fluid stream.

3. A coaxial stream delivery device comprising:
an inlet section comprising:
(i) an inner tubular wall extending along a longitudinal axis to define an inner lumen;
(ii) an outer tubular wall extending along the longitudinal axis concentrically about the inner tubular wall; and
(iii) N bridges extending radially between the inner tubular wall and the outer tubular wall to define N corresponding annular sector apertures, where the N is at least one; and
a source of cells coupled to an upstream end of the inner lumen;
a plenum chamber defined within a plenum wall that extends distally along the longitudinal axis from a distal end of the inlet section, the plenum chamber in fluid communication with the inner lumen and the N corresponding annular sector apertures;

wherein:
the N corresponding annular sector apertures provide longitudinal fluid communication between a first supply conduit coupled to a proximal end of the inlet section and the plenum chamber,
the inlet section is configured to receive a sheath fluid stream through the N corresponding annular sector apertures and to receive through the inner lumen a therapeutic fluid stream comprising cells from the source of cells, such that the sheath fluid stream shields the therapeutic fluid stream such that deleterious shear stress to the cells is prevented; and
further comprising a downstream sheath reduction apparatus configured such that a volume of the sheath fluid stream is removed from the therapeutic fluid stream via at least one exit port prior to delivery of the therapeutic fluid stream.

4. The coaxial stream delivery device of claim 3, wherein an inner radius of the outer tubular wall is substantially constant relative to the longitudinal axis.

5. The coaxial stream delivery device of claim 3, wherein an outer radius of the inner tubular wall is substantially constant relative to the longitudinal axis.

6. The coaxial stream delivery device of claim 3, wherein the N is at least two.

7. The coaxial stream delivery device of claim 3, wherein a total cross-sectional area of the N corresponding annular sector apertures is greater than a cross-sectional area of a distal end of the plenum chamber.

8. The coaxial stream delivery device of claim 3, wherein the therapeutic fluid stream exits the plenum chamber coaxially centered within the sheath fluid stream.

9. The coaxial stream delivery device of claim 3, wherein the therapeutic fluid stream comprises at least one non-cellular therapeutic agent.

10. The coaxial stream delivery device of claim 3, wherein the therapeutic fluid stream and the sheath fluid stream are dispensed from individual reservoirs by respective plungers.

11. The coaxial stream delivery device of claim 10, wherein the respective plungers are configured to be simultaneously actuated by a single lever.

12. The coaxial stream delivery device of claim 3, further comprising an outlet section extending along the longitudinal axis from a distal end of the plenum chamber and in fluid communication with the plenum chamber, the outlet section comprising an outlet lumen coaxial with the inner lumen and terminating in a luer fitting configured to connect a conduit in fluid communication with the outlet lumen.

13. The coaxial stream delivery device of claim 3, wherein a distal end of the inner lumen terminates proximal to the plenum chamber.

14. The coaxial stream delivery device of claim 3, wherein each of the N bridges monotonically decrease in thickness in a direction parallel to the longitudinal axis from the inlet section to the plenum chamber.

15. The coaxial stream delivery device of claim 3, wherein the inner tubular wall monotonically decreases in thickness in a direction parallel to the longitudinal axis from the inlet section to the plenum chamber.

16. The coaxial stream delivery device of claim 3, wherein a cross-section of each bridge of the N bridges, in a plane parallel to the longitudinal axis and normal to a radius along which each bridge of the N bridges extends from the longitudinal axis, is at least partially defined by opposing convex curves.

17. The coaxial stream delivery device of claim 3, wherein the downstream sheath reduction apparatus is downstream from an outlet section and comprises:

a second inlet section comprising an inlet lumen;

a second plenum chamber defined within a second plenum wall that extends distally along a second longitudinal axis from a distal end of the second inlet section, the second plenum chamber in fluid communication with the second inlet section; and a sheath flow reduction section comprising:

(i) a second inner tubular wall extending along the second longitudinal axis to define a second inner lumen;

(ii) a second outer tubular wall extending along the second longitudinal axis concentrically about the second inner tubular wall; and (iii) M bridges extending radially between the second inner tubular wall and the second outer tubular wall to define M corresponding annular sector apertures, where the M is at least one; and wherein:

the M corresponding annular sector apertures provide longitudinal fluid communication between the second plenum chamber and a first delivery conduit coupled to a distal end of the sheath flow reduction section, and an inner radius of the second plenum wall monotonically increases distally along the second longitudinal axis.

18. The coaxial stream delivery device of claim 17, wherein a cross-sectional area of the second inner lumen is greater than a cross-sectional area of the inner lumen.

19. The coaxial stream delivery device of claim 3, wherein an inner radius of the plenum wall monotonically decreases distally along the longitudinal axis.

* * * * *